(12) United States Patent
Myers et al.

(10) Patent No.: US 9,273,998 B2
(45) Date of Patent: Mar. 1, 2016

(54) ANALYSER

(71) Applicant: Oxford Instruments Industrial Products Limited, Oxfordshire (GB)

(72) Inventors: Richard Eric Myers, West Sussex (GB); Miika Heilio, Kirkkonummi (FI)

(73) Assignee: Oxford Instruments Industrial Products Limited (GB)

( * ) Notice: Subject to any disclaimer, the term of this patent is extended or adjusted under 35 U.S.C. 154(b) by 29 days.

(21) Appl. No.: 14/363,232

(22) PCT Filed: Dec. 6, 2012

(86) PCT No.: PCT/GB2012/000892
§ 371 (c)(1),
(2) Date: Jun. 5, 2014

(87) PCT Pub. No.: WO2013/083950
PCT Pub. Date: Jun. 13, 2013

(65) Prior Publication Data
US 2015/0292945 A1    Oct. 15, 2015

Related U.S. Application Data

(60) Provisional application No. 61/567,686, filed on Dec. 7, 2011.

(51) Int. Cl.
*G01J 3/30* (2006.01)
*G01J 3/10* (2006.01)
(Continued)

(52) U.S. Cl.
CPC ................. *G01J 3/10* (2013.01); *G01N 21/718* (2013.01); *G01J 3/02* (2013.01); *G01J 3/30* (2013.01); *G01J 3/4406* (2013.01); *G01N 2201/0612* (2013.01)

(58) Field of Classification Search
CPC ............. G01N 21/718; G01N 21/645; G01N 21/6458; G01J 3/02; G01J 3/10; G01J 3/30; G01J 3/4406

USPC .................................................. 356/300–445
See application file for complete search history.

(56) References Cited

U.S. PATENT DOCUMENTS

| | | | |
|---|---|---|---|
| 2008/0179541 A1* | 7/2008 | LeBoeuf ............ | G01N 21/6486 250/459.1 |
| 2012/0044488 A1 | 2/2012 | Senac | |

FOREIGN PATENT DOCUMENTS

| | | |
|---|---|---|
| CN | 1213432 A | 4/1999 |
| CN | 201053952 Y | 4/2008 |
| CN | 101268357 A | 9/2008 |

(Continued)

OTHER PUBLICATIONS

J. Cunat et al, "Man-Portable Laser-Induced Breakdown Spectroscopy System for in Situ Characterization of Karstic Formations", Applied Spectroscopy; Jan. 1, 2008; pp. 1250-1255.

(Continued)

*Primary Examiner* — Abdullahi Nur
(74) *Attorney, Agent, or Firm* — Blank Rome LLP

(57) ABSTRACT

A device (1) for analyzing the material composition of an object (2) has a casing (3) with a handle (4), an operating trigger (5), a window (6) for abutment against the object to be analyzed and a display (7) for displaying the analysis of the object. Mounted in the casing is a housing (11) having a base (12) to which it is pivotally connected about an axis (14) at one end (15). At the other end (16), a stepper motor (17) is provided for traversing the end across the base. This end has an opening (18) generally in alignment with an opening (19) in the housing in which the window is mounted. Within the housing, are mounted: a laser diode (21); a laser amplification crystal (22); a collimating lens (23); a laser focusing lens (24). The components are arranged on a laser projection axis (25), which passes out through the openings (18,19). A plane mirror (32) can receive light emitted by a plasma P excited at the surface of the object (2). Light from the plasma P is reflected in the direction (34) across the projection axis to a curved focusing mirror (35). From this mirror, the light is reflected again across the projection axis and focused on the end of an optical (fiber (37) set in an aperture (38) in the side wall (39) of the housing opposite from the reflecting mirror.

22 Claims, 4 Drawing Sheets

(51) Int. Cl.
  *G01N 21/71* (2006.01)
  *G01J 3/44* (2006.01)
  *G01J 3/02* (2006.01)

(56) References Cited

FOREIGN PATENT DOCUMENTS

| | | |
|---|---|---|
| EP | 0184590 A1 | 6/1986 |
| EP | 1936361 A1 | 6/2008 |
| JP | 2008256585 A | 10/2008 |
| WO | 2010061069 A1 | 6/2010 |

OTHER PUBLICATIONS

Agresti, J., et al. "Development and Application of a Portable LIPS Systems for Characterising Copper Alloy Artefacts", Analytical and Bioanalytical Chemistry, Springer, Berlin, DE., vol. 395, No. 7, Aug. 27, 2009; pp. 2255-2262.

B. Salle, et al., "Laser-Induced Breakdown Spectroscopy in Open-Path Configuration for the Analysis of Distant Objects", Spectrochimica, Acta, Part B, 62, 2007, pp. 739-768. w/English Abstract.

Z. Shu-Rui, et al., Introduction and Analysis of the Experimental Apparatus of the Laser-Induced Plasma', Chinese Journal of Spectroxopy Laboratory, vol. 26, No. 4, Jul. 2009, pp. 1046-1050. w/English Abstract.

Z. Lei, et al., "Research on Parameters Optimization of Laser-Induced Breakdown Spectroscopy Based Experimental Device", Spectroscopy and Spectral Analysis, vol. 31, No. 9, Sep. 2011, pp. 2355-2360. w/English Abstract.

* cited by examiner

ANALYSER

REFERENCE TO RELATED APPLICATIONS

The present application is a U.S. National Stage Application of PCT/GB2012/000892 filed Dec. 6, 2012 that claims benefit to U.S. Provisional Application No. 61/567,686, filed Dec. 7, 2011, whose disclosures are hereby incorporated by reference in their entirety into the present disclosure.

The present invention relates to a hand-held device for analysing the material composition of an object via plasma spectrum analysis.

It is known to analyse the material composition of objects, in typically metallic objects, by stimulating a plasma on their surface and spectrally analysing the plasma for the composition of the elements in the plasma corresponding to the elements in the object.

A number of devices are known in which a laser is projected through an aperture in a mirror for reflecting light from the plasma for analysis. We have sought to improve on this arrangement by dispensing with apertured mirrors.

The abstract of US 2012/0044488 is as follows:

A device for analyzing materials by plasma spectroscopy is of the portable and independent type, comprising a housing (10) containing a laser generator (18) that emits laser pulses that are focused on the surface of a material to be analyzed by means of a parabolic mirror (32) that is movable in translation inside the housing in order to perform a series of spot measurements along a scan line on the surface of the material to be analyzed and in order to take a measurement from a calibration sample (50) mounted in the measurement endpiece (22) of the housing (10).

This arrangement is complex, using many mirrors and reflecting the laser and plasma light with the same mirrors, which we prefer not to do.

The abstract of the Japanese equivalent, JP61086636, of EP 0,176,625 includes:

A laser oscillator 22 is controlled by a switching circuit 24. Infrared-ray pulse laser light A is projected on the surface of a sample 10 from the laser oscillator 22 so that energy density becomes 2.0×10<9>W/mm<2> or more. Excited and discharged light B is converged to a mirror 12 at a solid cubic angle 16 deg. in a light guiding system in a case 18 through a path wherein an inactive gas atmosphere is maintained. The image of the light is formed at an input slit 16A of a spectroscope 16.

This arrangement is bulky and does not lend itself to a hand-held device.

The object of the present invention is to provide an improved hand-held device for analysing the material composition of an object via plasma spectrum analysis.

According to the invention there is provided a hand-held device for analysing the material composition of an object via plasma spectrum analysis, the device comprising:

a manually held casing;
a laser housing within the casing;
a laser within the housing, the laser having a projection axis;
openings in the housing and the casing through which a beam from the laser can be projected onto an object to be analysed with the establishment of a plasma at a surface of the object;
a first mirror mounted in the housing for receiving plasma emitted light within the openings via the openings, the mirror being to one side of the projection axis with its normal axis acutely angled to the projection axis for the plasma light to the other side of the projection axis;
a second, focusing mirror mounted in the housing for receiving the plasma light reflected by the first mirror and reflecting it back again to the first side of the projection axis, the focusing mirror being angled with a central normal axis more acutely angled to the projection axis than the first mirror; and
a receptor for passing the plasma light to a spectral analyser.

Whilst we can envisage that the first mirror is substantially planar, it could be curved to a degree less than the second mirror for preliminary focus of the plasma device, normally it will be planar for practical purposes. Normally the device includes an abutment surface for determining a spacing of the object to be analysed from the housing and the first mirror will be so mounted in the laser housing to receive a divergent beam—a pyramidal beam when the mirror is rectangular—of plasma light having a central axis set at between 7 ½° and 20° and preferably between 10° and 15° to the projection axis. The first mirror is mounted in the body at an angle to take account of this angle of the plasma beam and the position of the second mirror. In the preferred embodiment the extent of the first mirror axially of the projection axis overlaps with the axial extent of the second mirror. For such an arrangement, the first mirror is preferably set with its normal axis at between 25° and 40° to the projection axis and preferably between 30° and 35° . However, where the second mirror is positioned further from the openings towards the laser, the first mirror can be set with it s normal axis at between 15° and 30° to the projection axis. Whereas, the central normal axis of the second mirror could be substantially perpendicular to the projection axis, whereby twice reflected, convergent focused plasma light will cross the projection axis at the same mean angle as it crossed from the first mirror, this is not appropriate where the mirrors axially overlap. In such a case, the second mirror is preferably angled to reflect the plasma beam further towards the laser than the edge of the first mirror. For this the second mirror is angled with its central normal axis at between 10° and 20° to the perpendicular to the projection axis. It can also be envisaged that the second mirror could be further to the laser and angled to direct the reflected beam substantially perpendicularly to the projection axis. For this the same angular range is envisaged but with the opposite sign.

Normally the laser will have a diode—mounted in the housing remote from its opening, an amplification crystal, a collimating lens and a focusing lens. Typically the laser is operated as a passively Q-switched pulsed laser. Whilst it is envisaged that the focusing lens could be arranged between the two crossings of the reflected light across the projection axis, it is preferable arranged on the side of the second crossing remote from the openings.

In the preferred embodiment, the receptor is an optical fibre for passing the plasma light to the spectral analyser itself mounted in the casing. In this case the focal length of the second mirror will be such to bring the reflected plasma light to focus on the end of the optical fibre, which can be arranged in wall of the housing opposite from the second mirror.

Advantageously the housing is movably mounted in the casing, whereby the point of incidence of the laser beam along the projection axis on the object to be analysed can be traversed by controlled movement of the housing. This can be in translation, but is preferably in rotation. In the preferred embodiment, the housing is pivotally mounted to the casing at its laser diode end and its opening end is traversable with respect to the casing under control of an actuator, preferably a stepper motor.

Typically the device is for the analysis of metals, however the device may be for the analysis of other materials such as plastics or any other type of material.

To help understanding of the invention, a specific embodiment thereof will now be described by way of example and with reference to the accompanying drawings, in which.

Figure 1:
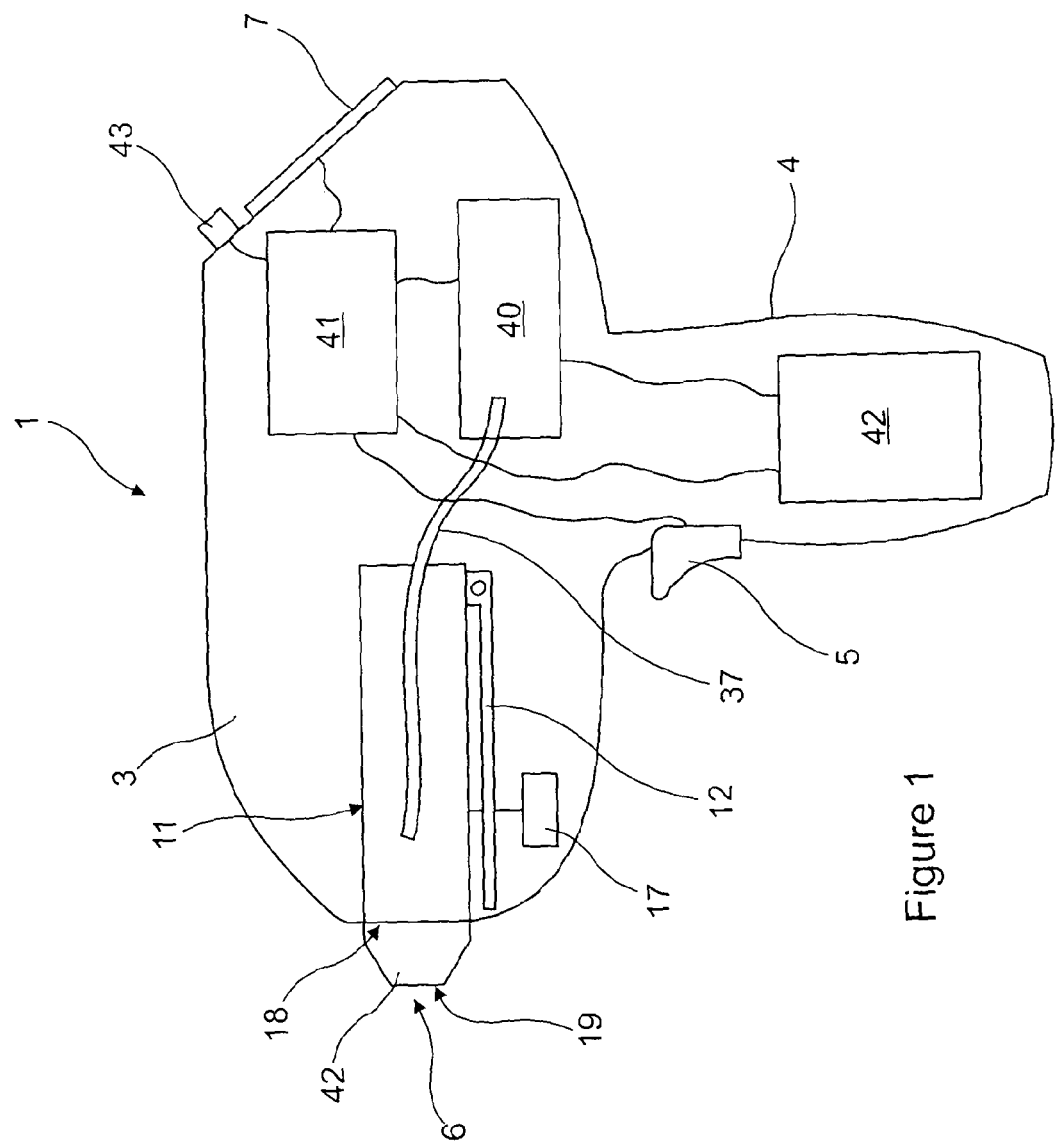
FIG. 1 is a cross-sectional side view diagram of an analyser of the present invention.
Figure 2:
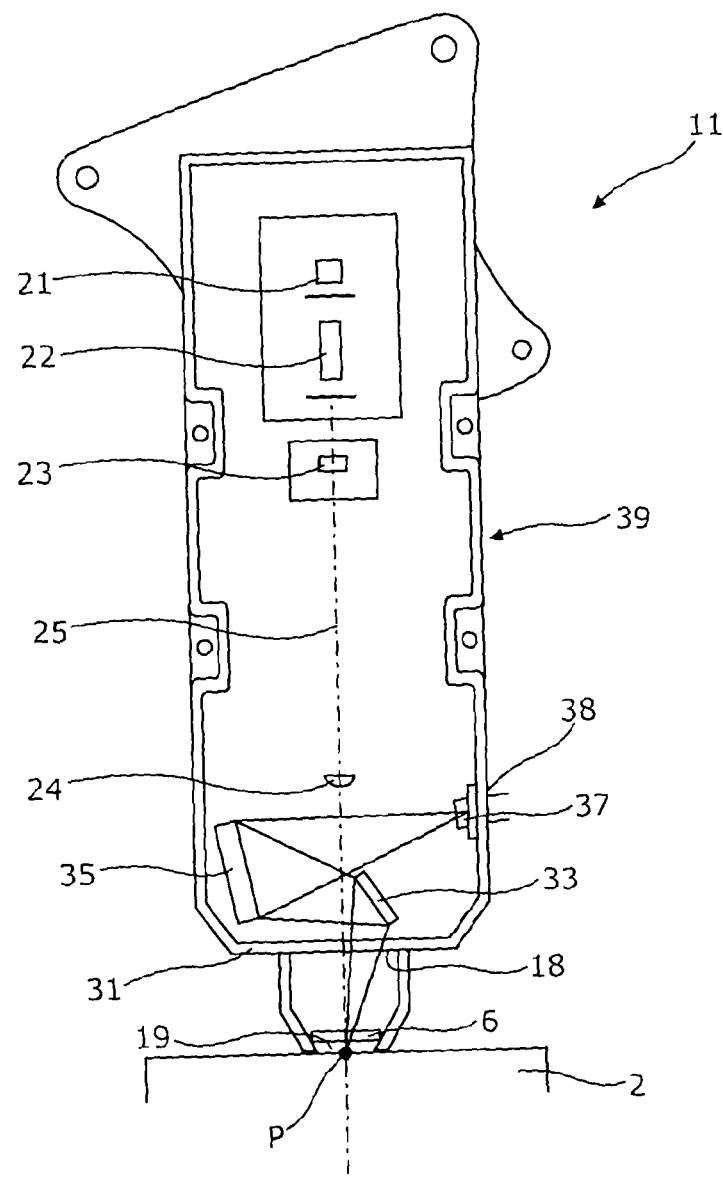
FIG. 2 is a plane view of a laser housing of the analyser of FIG. 1 with the lid removed.
Figure 3:
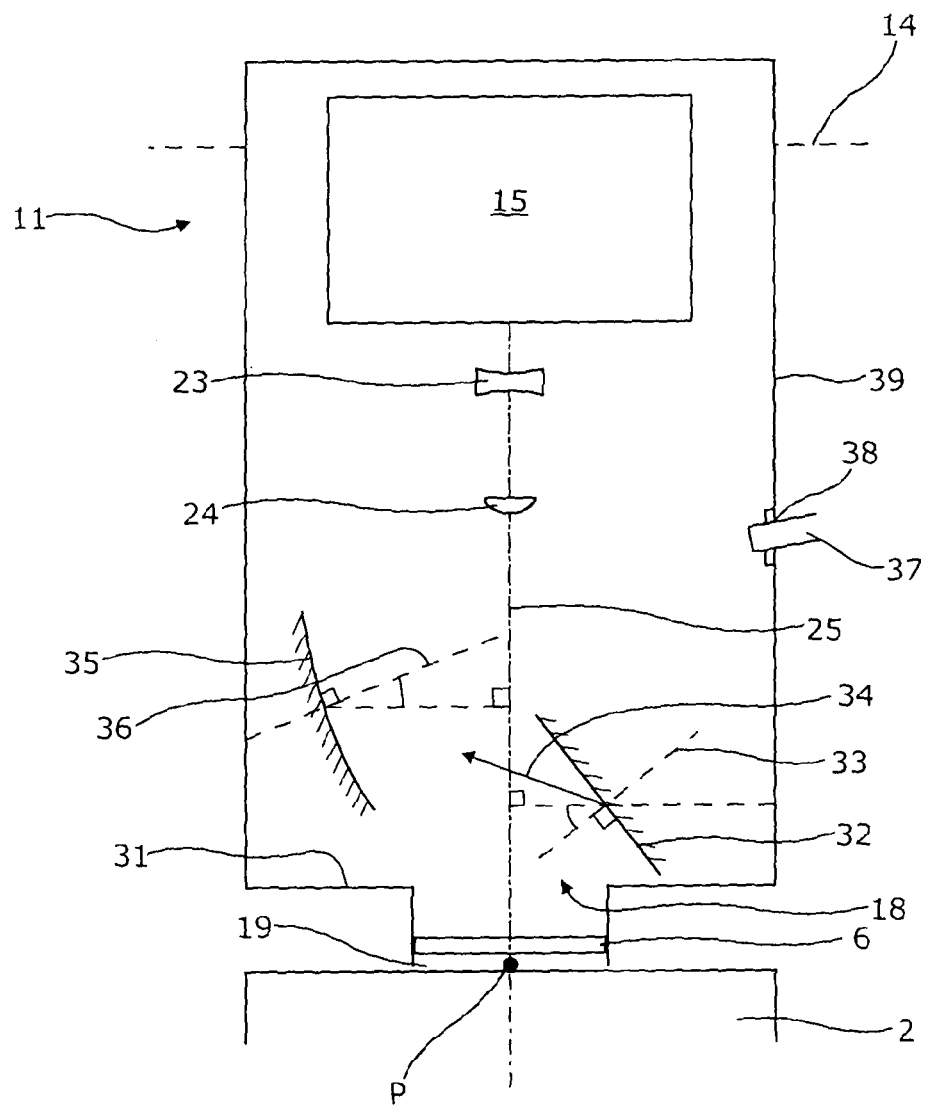
FIG. 3 is a plane view diagram of the laser housing of FIG. 2.
Figure 4:
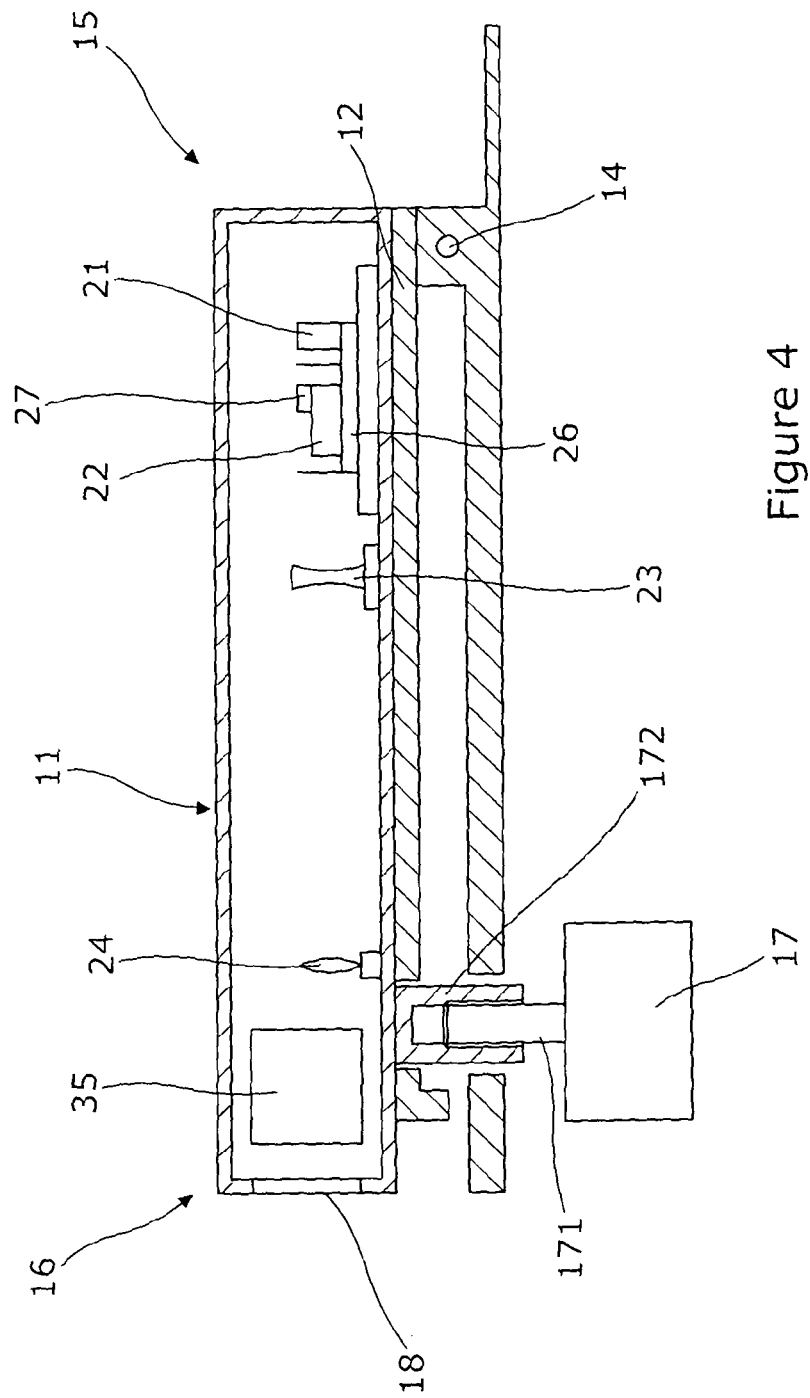
FIG. 4 is a cross-sectional side view of the laser housing of FIG. 2 along projection axis 25.

Referring to the drawings a device 1 for analysing the material composition of an object 2 has a casing 3 with a handle 4, an operating trigger 5, a window 6 for abutment against the object to be analysed and a display 7 for displaying the analysis of the object.

Mounted in the casing is a housing 11 having a base 12 to which it is pivotally connected about an axis 14 at one end 15. At the other end 16, a stepper motor 17 is provided for traversing the end across the base. Threaded bolt 171 extends into threaded nut 172 mounted to the base 12, and is rotatable by stepper motor 17 to raise and lower the housing 11. End 16 has an opening 18 generally in alignment with an opening 19 in the housing in which the window is mounted.

Within the housing, which is a light tight aluminium box, are mounted:
a laser diode 21 at the end 15
a laser amplification crystal 22, mounted on a Peltier device 26 for its cooling to the housing 11 and carrying a resistor 27 for its heating
a collimating lens 23
a laser focusing lens 24.

The components are arranged on a laser projection axis 25, which passes out through the openings 18,19.

Inside an end wall 31, having the opening 18, to one side of the axis 25 is provided a plane mirror 32. It is in partial alignment with the opening, yet it is clear of the laser projection axis. In this position, it can receive light emitted by a plasma P excited on the object 2. It is set with its normal axis 33 at 33° to the perpendicular to the projection axis, i.e. with its plane at 33° to the projection axis. Light from the plasma P is reflected in the direction 34 across the projection axis to a curved focusing mirror 35. This is set with its central normal axis 36 set at 19° to the perpendicular to the projection axis. From this mirror, the light is reflected again across the projection axis and focused on the end of an optical fibre 37 set at 15° to the normal to the projection axis in an aperture 38 in the side wall 39 of the housing opposite from the reflecting mirror.

The optical fibre leads to a spectral analyser 40 in the casing.

The device has a controller 41, a power supply 42 and an ON/OFF switch 43. Switching on sets the controller to power the laser diode 21 at lower power and the resistor 24, to bring the diode and the amplified crystal to quiescent temperature. When operation is initiated by action on the trigger, provided that a proximity sensor 42 adjacent the window detects the presence of the object 2. As soon as the laser diode and the crystal are at operating temperature a pulsed laser beam is projected and the plasma is established. In operation, the laser diode 21 and laser amplification crystal 22, amongst other components, comprise a passively Q-switched, pulsed laser. The analyser analyses the constituent elements of the object 2 in real time. The laser is typically pulsed at between 3-5 kHz with pulses of approximately 30-50 µJ. Such pulse power and frequency permits spectral analysis of the plasma light by the spectrometer 40 to continue throughout the laser pulse cycle. The stepper motor traverses the laser beam whereby successive analyses of the constituent elements can be made. Should the traversing result in no plasma light being analysed, as when a discontinuity in the object such as a hole is encountered, the direction of traverse is reversed so that previous measurements can be repeated and/or the rate traversing is reduced to increase the plasma light collection.

Once a consistent analysis has been determined, the result is displayed on the display and the controller controls the analyser in its quiescent state.

The invention claimed is:

1. A hand-held device for analysing the material composition of an object via plasma spectrum analysis, the device comprising:
a manually held casing;
a laser housing within the casing;
a laser within the housing, the laser having a projection axis;
openings in the housing and the casing through which a beam from the laser can be projected onto an object to be analysed with the establishment of a plasma at a surface of the object;
a first mirror mounted in the housing for receiving plasma emitted light within the openings, via the openings, the mirror being to one side of the projection axis with its normal axis acutely angled to the normal to the projection axis for reflection of the plasma light to the other side of the projection axis;
a second, focusing mirror mounted in the housing for receiving the plasma light reflected by the first mirror and reflecting it back again to the first side of the projection axis, the focusing mirror being angled with a central normal axis more acutely angled to the normal to the projection axis than the first mirror; and
a receptor for receiving the plasma light from the second mirror and for passing the plasma light to a spectral analyser.

2. A device as claimed in claim 1, wherein the first mirror is a focusing mirror, which is curved less than the second mirror for preliminary focus of the plasma device.

3. A device as claimed in claim 1, wherein the first mirror is a substantially planar mirror.

4. A device as claimed in claim 1, wherein the device includes an abutment surface for determining a spacing of the object to be analysed from the housing.

5. A device as claimed in claim 4, wherein the first mirror is so mounted and arranged in the laser housing to receive a divergent beam of plasma light from an abutted object, via the openings, the divergent beam having a central axis set at between 7 ½° and 20° to the projection axis.

6. A device as claimed in claim 5, wherein the arrangement is such that the central axis of the beam of plasma light at the openings is angled at between 10° and 15° to the projection axis.

7. A device as claimed in claim 1, wherein the extent of the first mirror axially of the projection axis overlaps with the axial extent of the second mirror.

8. A device as claimed in claim 7, wherein the first mirror is mounted to the laser housing with its normal axis angled at between 25° and 40° to the perpendicular to the projection axis.

9. A device as claimed in claim 8, wherein the arrangement is such that the normal axis of the first mirror is angled at between 30° and 35° to the perpendicular to the projection axis.

10. A device as claimed in claim 7, wherein the second mirror is angled with its central normal axis at between 10° and 20° to the perpendicular to the projection axis.

11. A device as claimed in claim 1, wherein the second mirror is arranged such that the extent of the first mirror axially of the projection axis does not overlap the second mirror.

12. A device as claimed in claim 11, wherein the first mirror is mounted to the laser housing with its normal axis angled at between 15° and 30° to the perpendicular to the projection axis.

13. A device as claimed in claim 11, wherein the second mirror is angled with its central normal axis substantially perpendicular to the projection axis.

14. A device as claimed in claim 1, wherein the laser comprises:
 a diode, mounted to the housing remote from its opening;
 an amplification crystal;
 a collimating lens or lenses; and
 a focusing lens.

15. A device as claimed in claim 14, wherein the focusing lens is arranged between a first crossing of the plasma light, reflected from the first mirror, and the projection axis and a second crossing of the plasma light, reflected from the second mirror, and the projection axis.

16. A device as claimed in claim 14, wherein the focusing lens is arranged between the collimating lens and a crossing of the plasma light reflected from the second mirror and the projection axis.

17. A device as claimed in claim 1, wherein the receptor is an optical fibre.

18. A device as claimed in claim 1, wherein the laser housing is movably mounted in the casing, whereby the point of incidence of the laser beam on the object to be analysed can be traversed by controlled movement of the housing.

19. A device as claimed in claim 18, wherein the laser housing is translatable with respect to the casing.

20. A device as claimed in claim 18, wherein the laser housing is rotatable with respect to the casing.

21. A device as claimed in claim 20, wherein the laser housing is pivotally mounted to the casing at its laser diode end and its opening end is traversable with respect to the casing under control of an actuator.

22. A device as claimed in claim 21, wherein the actuator is a stepper motor.

* * * * *